US 8,611,990 B2

(12) United States Patent
Richardson (10) Patent No.: US 8,611,990 B2
(45) Date of Patent: Dec. 17, 2013

(54) SYSTEMS, METHODS AND COMPUTER PROGRAM PRODUCTS FOR HEART MONITORING

(75) Inventor: Charles L. Richardson, Monroe, NC (US)

(73) Assignee: Lifescience Solutions LLC, Charlotte, NC (US)

( * ) Notice: Subject to any disclaimer, the term of this patent is extended or adjusted under 35 U.S.C. 154(b) by 31 days.

(21) Appl. No.: 13/035,259

(22) Filed: Feb. 25, 2011

(65) Prior Publication Data

US 2011/0152705 A1    Jun. 23, 2011

Related U.S. Application Data

(63) Continuation of application No. 11/072,463, filed on Mar. 7, 2005, now Pat. No. 7,917,195.

(60) Provisional application No. 60/550,533, filed on Mar. 5, 2004.

(51) Int. Cl.
*A61B 5/0402* (2006.01)

(52) U.S. Cl.
USPC ........... 600/509; 600/508; 600/510; 600/513; 600/523; 600/546; 607/1; 607/2; 607/60; 607/115

(58) Field of Classification Search
USPC .......... 600/508–510, 513, 523, 546; 607/1–2, 607/60, 115
See application file for complete search history.

(56) References Cited

U.S. PATENT DOCUMENTS

| | | |
|---|---|---|
| 3,302,639 A | 2/1967 | Koffler |
| 3,523,539 A | 8/1970 | Lavezzo et al. |
| 3,662,758 A | 5/1972 | Glover |
| 3,669,120 A | 6/1972 | Nielsen |
| 3,835,865 A | 9/1974 | Bowers |
| 3,925,041 A | 12/1975 | Patterson et al. |
| 3,985,142 A | 10/1976 | Wickham |
| 4,114,627 A | 9/1978 | Lewyn et al. |
| 4,492,235 A | 1/1985 | Sitrick |
| 4,531,527 A | 7/1985 | Reinhold, Jr. et al. |
| 4,821,724 A | 4/1989 | Whigham et al. |
| 5,090,418 A | 2/1992 | Squires et al. |

(Continued)

FOREIGN PATENT DOCUMENTS

| | | |
|---|---|---|
| WO | 0040148 A1 | 7/2000 |
| WO | WO-2008/029362 A2 | 3/2008 |

OTHER PUBLICATIONS

Office Action for Chinese Application No. 2008800215701 issued Feb. 11, 2011.

*Primary Examiner* — Deborah Malamud
(74) *Attorney, Agent, or Firm* — Tarolli, Sundheim, Covell & Tummino LLP (57) ABSTRACT

The present invention provides systems, methods and computer program products for monitoring a heart. According to one embodiment, the system includes an implantable registering unit. The registering unit comprises a first controller structured to register an electrical signal from the heart. The system includes a second controller in operable communication with the first controller. The second controller comprises a data repository structured to receive data corresponding to the registered electrical signal and being structured to store the data. The data repository stores data corresponding to a baseline electrical signal of the heart. The second controller is structured to receive the data from the first controller corresponding to the registered electrical signal and to compare the registered electrical signal to the baseline electrical signal to determine whether the heart is functioning properly.

19 Claims, 4 Drawing Sheets

(56) References Cited

U.S. PATENT DOCUMENTS

| | | |
|---|---|---|
| 5,092,343 A | 3/1992 | Spitzer et al. |
| 5,139,028 A | 8/1992 | Steinhaus et al. |
| 5,139,668 A | 8/1992 | Pan et al. |
| 5,161,540 A | 11/1992 | Mueller |
| 5,197,480 A | 3/1993 | Gebhardt |
| 5,246,008 A | 9/1993 | Mueller |
| 5,411,031 A | 5/1995 | Yomtov |
| 5,782,890 A | 7/1998 | Wahlstrand et al. |
| 5,820,659 A | 10/1998 | Ekiner et al. |
| 5,833,623 A | 11/1998 | Mann et al. |
| 6,044,294 A | 3/2000 | Mortazavi et al. |
| 6,198,965 B1 | 3/2001 | Penner et al. |
| 6,234,973 B1 | 5/2001 | Meador et al. |
| 6,269,264 B1 | 7/2001 | Weyant et al. |
| 6,411,840 B1 | 6/2002 | Bardy |
| 6,424,860 B1 | 7/2002 | Karlsson et al. |
| 6,473,638 B2 | 10/2002 | Ferek-Petric |
| 6,740,636 B2 | 5/2004 | Horuk |
| 6,745,076 B2 | 6/2004 | Wohlgemuth et al. |
| 6,824,592 B2 | 11/2004 | Monzyk et al. |
| 6,983,183 B2 | 1/2006 | Thiagarajan et al. |
| 7,277,754 B2 | 10/2007 | McCabe et al. |
| 2002/0198445 A1 | 12/2002 | Dominguez et al. |
| 2003/0158466 A1 | 8/2003 | Lynn et al. |
| 2003/0163057 A1 | 8/2003 | Flick et al. |
| 2005/0027323 A1 | 2/2005 | Mulligan et al. |
| 2005/0049474 A1 | 3/2005 | Kellogg et al. |
| 2005/0113703 A1 | 5/2005 | Farringdon et al. |
| 2005/0234360 A1 | 10/2005 | Richardson |
| 2007/0062870 A1 | 3/2007 | Chen et al. |
| 2007/0156030 A1 | 7/2007 | Richardson |
| 2007/0179392 A1 | 8/2007 | Zhang |
| 2007/0191722 A1 | 8/2007 | Richardson et al. |

— Original Template
---- Follow Up Template
/// Area Of Discrepancy
(For Comparison Of % Match)

Fig. 4

— Original Template
---- Follow Up Template
• Point Comparison Model
(For Comparison Of % Match)

SYSTEMS, METHODS AND COMPUTER PROGRAM PRODUCTS FOR HEART MONITORING

CROSS REFERENCE TO RELATED APPLICATIONS

This application is a continuation of U.S. application Ser. No. 11/072,463, filed Mar. 7, 2005, now U.S. Pat. No. 7,917,195 which claims the benefit of U.S. Provisional Application No. 60/550,533, filed Mar. 5, 2004, and which issued as U.S. Pat. No. 7,917,195, and all of which are hereby incorporated by reference in their entireties.

FIELD OF THE INVENTION

The present invention relates generally to medical apparatus and methods for monitoring and evaluating cardiac function and, more particularly, to non-invasive apparatus and methods for monitoring and evaluating the cardiac function of heart transplant and congestive heart failure patients, detecting heart failure in such patients and providing an appropriate warning to the patient and/or physician in the event of actual or anticipated heart failure, and/or administering therapeutic drugs to the patient to treat the patient's condition.

BACKGROUND OF THE INVENTION

Cardiovascular disease if the leading cause of death for both men and women in the U.S. today and claims more lives each year than the next five leading causes of death combined.

In the United States, nearly 5 million patients have been diagnosed with heart failure. Each year more than 500,000 new cases are recognized. This represents, by far the fastest growing area of cardiology. As many as 20% of these patients qualify for an implanted device, either an implantable pacemaker or implantable cardiac defibrillator ("ICD") or a biventricular pacemaker/ICD, and a fortunate percent of those severely symptomatic individuals will go on to cardiac transplant.

The primary diagnoses associated with heart transplantation are coronary artery disease (45%) and cardiomyopathy (45%), with congenital heart disease accounting for 8% and approximately 3% for retransplantation.

Each year approximately 2,500 cardiac transplants are performed in the United States and this number approaches 5,000 worldwide. One-year survival is approximately 85% in experienced transplant centers, with a five-year survival rate approaching approximately 70%. The most common cause of death is infection, followed by acute rejection. Although technology exists to treat bradycardia and tachycardia, i.e., pacemakers and defibrillators, respectively, the currently available apparatus and methods for monitoring a transplanted heart or for assisting in congestive heart failure assessment are quite limited and, for the most part, require the patient to undergo extensive invasive procedures or repetitive visits to a hospital or other medical facility which can be expensive.

Known methods for monitoring patients who receive a heart transplant generally involve an invasive procedure called endomyocardial biopsy ("EMB"). EMB procedures typically require an invasive biopsy of the transplanted heart in which the patient is taken to a catheterization laboratory and a large blood vessel (usually in the neck) is cannulated allowing a biopsy catheter to be advanced into the right side of the heart. Several small pieces or bites of the myocardium are sampled during the EMB, which are then sent for pathological evaluation. Similar invasive procedures are required of patients suffering from congestive heart failure, including catheterization to evaluate pressures inside the heart.

As discussed above, the rejection of a transplanted heart by the patient's body is one of the leading causes of death during the first year following the transplant. In order to detect early rejection of a transplanted heart, multiple EMBs are performed at regular, predetermined intervals. The typical patient undergoes up to twenty (20) EMBs during the first year. After the first year, even patients who have not experienced a rejection episode continue to require periodic EMBs to insure normal function of the transplanted heart. Although EMBs detect rejection and allow treatment in order to prevent death of the transplant patient, EMBs themselves result in a substantial risk of bleeding, infection, cardiac perforation, and other morbidities including death. In addition, this catheterization procedure is not only costly, but also painful and inconvenient for the patient.

Medical practitioners have attempted to reduce the risks associated with EMBs by exploring alternative methods for predicting transplant rejection and/or complications from congestive heart failure. For example, during the last decade investigators in Europe focused on intramyocardial electrograms and immune system markers that had the potential for predicting ischemia as well as acute transplant rejection. In studies on canines evaluating data from four myocardial sites, it was found that analysis of the mean intramyocardial unipolar peak-to-peak R-wave amplitude had a sensitivity (i.e., an ability to identify rejection) and a specificity (i.e., percentage of false positives) sufficient for diagnosing most transplant rejection. It also was discovered that, as the number of myocardial leads increases (i.e., the number of myocardial sites monitored increases), the sensitivity of detecting transplant rejection also increased. Preliminary studies on humans were able to show a correlation between acute rejection episodes and the mean amplitude of the R-wave of the QRS complex.

Over the past fifteen years, more than one thousand prototype unipolar, peak-to-peak rejection monitors ("UPPRMs") have been implanted in both adults and children. UPPRMs require two or more electrodes attached to the patient's heart that are structured to register QRS voltage. The amplitude measurement of the intramyocardial electrogram ("IMEG") was used to predict rejection.

Another method of conventional rejection monitoring is disclosed in U.S. Pat. No. 5,246,008 to Mueller, which is incorporated herein. As disclosed in Mueller, the rejection monitor ("RM") or telemetry measuring unit preferably is connected to the patient's heart using two pairs of current and measuring electrodes in which each current electrode is annularly surrounded by a measuring electrode. This RM includes a miniaturized, battery-operated electronic measuring circuit for impedance measurement. The RM also has a transmitter-receiver circuit for electromagnetic waves with a carrier frequency of one coil being able to function as the antenna. An AC voltage is applied in a square-wave pulse to the tissue via the current electrodes. The impedance of the body tissue, is then measured via the measuring electrodes. The receiver coil of a telemetry control unit can be disposed on the body of the patient over the RM, preferably during the night rest periods.

The control unit transmits an ON signal via the receiver coil to the RM via the antenna. The RM then begins applying AC voltage in a square-wave pulse utilizing the current electrodes and measuring the impedance via the measuring electrodes. The RM transmits the measured values for a predetermined measuring duration via the induction coupling formed by the antenna and receiver coil to the control unit. The measured values are stored by the control unit, such as on a computer, and values can be called in by a clinic using a modem via a telephone line.

As disclosed in Mueller, the impedance consists substantially of the ohmic resistance and a capacitive reactance. The ohmic resistance depends substantially on the extracellular space of the tissue, whereas the capacitive reactance depends substantially on the properties of the cell membrane. As a result of ischemia of the tissue during a rejection reaction, intracellular edema with simultaneous shrinkage of the extracellular space occurs, which results in changes to the ohmic resistance and capacitive reactance of the tissue. The change of the pulse form of the ac voltage is a measure of the impedance. If a square-pulse voltage is used as the ac voltage, the change of the pulse height corresponds to the ohmic resistance, whereas the change in the steepness of the leading edges of the square-wave pulses is a measure of the capacitive reactance.

Results have suggested several advantages of these alternative methods over current methods of transplant rejection assessment such as EMBs. In particular, UPPRMs enabled reliable recognition of transplant rejection episodes at an early stage, thus allowing prompt treatment to reverse rejection and to block further development to more severe stages. Because advanced stages of transplant rejection were not encountered, the amount of additional immuno-suppression necessary to terminate rejection was moderate thereby reducing the treatment costs. Compared to an eighty-five percent (85%) survival rate for one-year post transplant when EMBs are used to assess transplant rejection, there were no deaths from acute transplant rejection when UPPRMs was used to assess rejection, provided the patient adhered strictly to short-interval, and preferably daily, IMEG recording. Biopsy findings showed the IMEGs to have one hundred percent (100%) sensitivity and ninety-seven percent (97%) specificity in detecting transplant rejection and there were 3% false negatives. In those few cases when the UPPRMs indicated transplant rejection with negative biopsy results (reason for less than one hundred percent (100%) specificity), all of these patients went on to have transplant rejection within twenty-four (24) to forty-eight (48) hours.

However, simple IMEG amplitude measurement is subject to variation due to the patient's daily rhythm, exercise status, and medications. A drop in amplitude may not always correlate to a rejection reaction. Moreover, because conventional UPPRMs provide at best only periodic monitoring (i.e., only while the patient is sleeping) the IMEG data registered by the UPPRMs does not provide the best data for determining a rejection reaction.

In light of the foregoing, it would be highly desirable to provide methods and apparatus capable of eliminating the risks associated with EMBs while at the same time providing more comprehensive data regarding the function of a patient's heart. Specifically, the methods and apparatus should allow for continuous, non-invasive monitoring of a patient's heart to thereby accurately detect heart rejection or failure at its earliest phase. In addition, the apparatus and methods should preferably enable medical personnel to obtain historic and real-time monitoring data and information about the patient's heart so that the medical personnel can more effectively diagnose, discuss, coordinate or alter the patient's treatment.

SUMMARY OF THE INVENTION

The present invention provides non-invasive apparatus and a method for monitoring and evaluating the cardiac function of heart transplant and congestive heart failure patients, detecting heart failure in such patients and providing an appropriate warning to the patient and/or physician in the event of actual or anticipated heart failure, and/or administering therapeutic drugs to the patient to treat the patient's condition.

According to one embodiment, the apparatus for monitoring a patient's heart includes a registering unit structured to be implanted into the patient's body. The registering unit includes a first controller in electrical communication with the patient's heart. The first controller is structured to register an electrical signal from the patient's heart. The apparatus includes a second controller in operable communication with the first controller of the registering unit. The second controller includes a data repository structured to receive data corresponding to the registered electrical signal and structured to store the data. The data repository of the second controller stores data corresponding to a baseline electrical signal of the patient's heart. The second controller is structured to receive the data from the first controller corresponding to the registered electrical signal. In one construction, the registering unit includes a transmitter in operable communication with the second controller. In another construction, the registering unit is in at least one of electrical or optical communication with the second controller. In still another construction, the data repository electrically or magnetically stores the data corresponding to the registered electrical signal.

According to another embodiment, the apparatus includes a relay unit in operable communication with the first controller of the registering unit. The relay unit is structured to receive data from the first controller corresponding to the registered electrical signal. The apparatus includes a second controller in operable communication with the relay unit. The second controller includes a data repository structured to receive data from the relay unit corresponding to the registered electrical signal and structured to store the data. The data repository of the second controller stores data corresponding to a baseline electrical signal of the patient's heart. The second controller is structured to receive the data from the relay unit corresponding to the registered electrical signal.

In one construction, the registering unit further comprises a transmitter in operable communication with the relay unit. In another construction, the registering unit is in at least one of electrical or optical communication with the relay unit. In another embodiment, the relay unit communicates with the second controller via a computer network.

The second controller is structured to compare the registered electrical signal to the baseline electrical signal to determine whether the patient's heart is functioning properly. According to one construction, the second controller is structured to generate a first template corresponding to the baseline electrical signal and a second template corresponding to the registered electrical signal. The second controller is structured to measure the area between the first template and the second template to determine whether the patient's heart is functioning properly. In another construction, the second controller is structured to identify a plurality of comparison points for the first template and to identify a plurality of comparison points for the second template. Each of the plurality of comparison points for the second template corresponds to one of the comparison points for the first template. The second controller is further structured to measure differences between each of the corresponding plurality of comparison points for the first template and the second template to determine whether the patient's heart is functioning properly.

The present invention also provides a computer program product for monitoring a patient's heart. The computer program product includes a computer-readable storage medium having computer-readable program code portions stored therein. According to one embodiment, the computer-readable program portions include an executable portion for receiving data representing a registered electrical signal from the patient's heart and a baseline electrical signal of the patient's heart. The executable portion compares the registered electrical signal to the baseline electrical signal to determine whether the patient's heart is functioning properly. In one form, the executable portion generates a first template corresponding to the baseline electrical signal and a second template corresponding to the registered electrical signal. The executable portion then measures the area between the first template and the second template to determine whether the patient's heart is functioning properly. In another form, the executable portion identifies a plurality of comparison points for the first template and identifies a plurality of comparison points for the second template. Each of the plurality of comparison points for the second template corresponds to one of the comparison points for the first template. The executable portion measures differences between each of the corresponding plurality of comparison points for the first template and the second template to determine whether the patient's heart is functioning properly.

The present invention also provides a method for monitoring a patient's heart. According to one embodiment, the method includes implanting a registering unit into a patient's body. At least one pair of electrodes is implanted into the patient's body in electrical communication with the patient's heart. The method includes registering an electrical signal from the patient's heart. Data corresponding to the registered electrical signal is communicated from a first controller to a second controller. In one form, the data representing the registered electrical signal is stored in computer-readable memory.

The method includes comparing the registered electrical signal to a baseline electrical signal to determine whether the patient's heart is functioning properly. In one form, the comparing step includes generating a first template corresponding to the baseline electrical signal. A second template corresponding to the registered electrical signal is generated. Thereafter, the area between the first template and the second template is measured to determine whether the patient's heart is functioning properly. In another form, the comparing step includes identifying a plurality of comparison points for both the first template and second template. Each of the plurality of comparison points for the second template corresponds to one of the comparison points for the first template. The differences between each of the corresponding plurality of comparison points for the first template and the second template are then measured to determine whether the patient's heart is functioning properly.

Thus, there is provided methods and apparatus capable of eliminating the risks associated with EMBs while at the same time providing more comprehensive data regarding the function of a patient's heart. These methods and apparatus allow for accurate, non-invasive monitoring of a patient's heart to thereby detect heart rejection or failure at its earliest phase. In addition, the apparatus and methods enable medical personnel to obtain historic and real-time monitoring data and information about the patient's heart so that the medical personnel can more effectively diagnose, discuss, coordinate or alter the patient's treatment.

BRIEF DESCRIPTION OF THE DRAWINGS

The foregoing and other advantages and features of the invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale.

Six figures have been selected to illustrate the present invention.

DESCRIPTION OF THE PREFERRED EMBODIMENTS

The present invention will now be described more fully hereinafter with reference to the accompanying drawings, in which some, but not all embodiments of the invention are shown. Indeed, these embodiments of the invention may take many different forms and should not be construed as limited to the embodiments set forth herein; rather, these embodiments are provided so that this disclosure will satisfy applicable legal requirements. Like numbers refer to like elements throughout.

Figure 1:
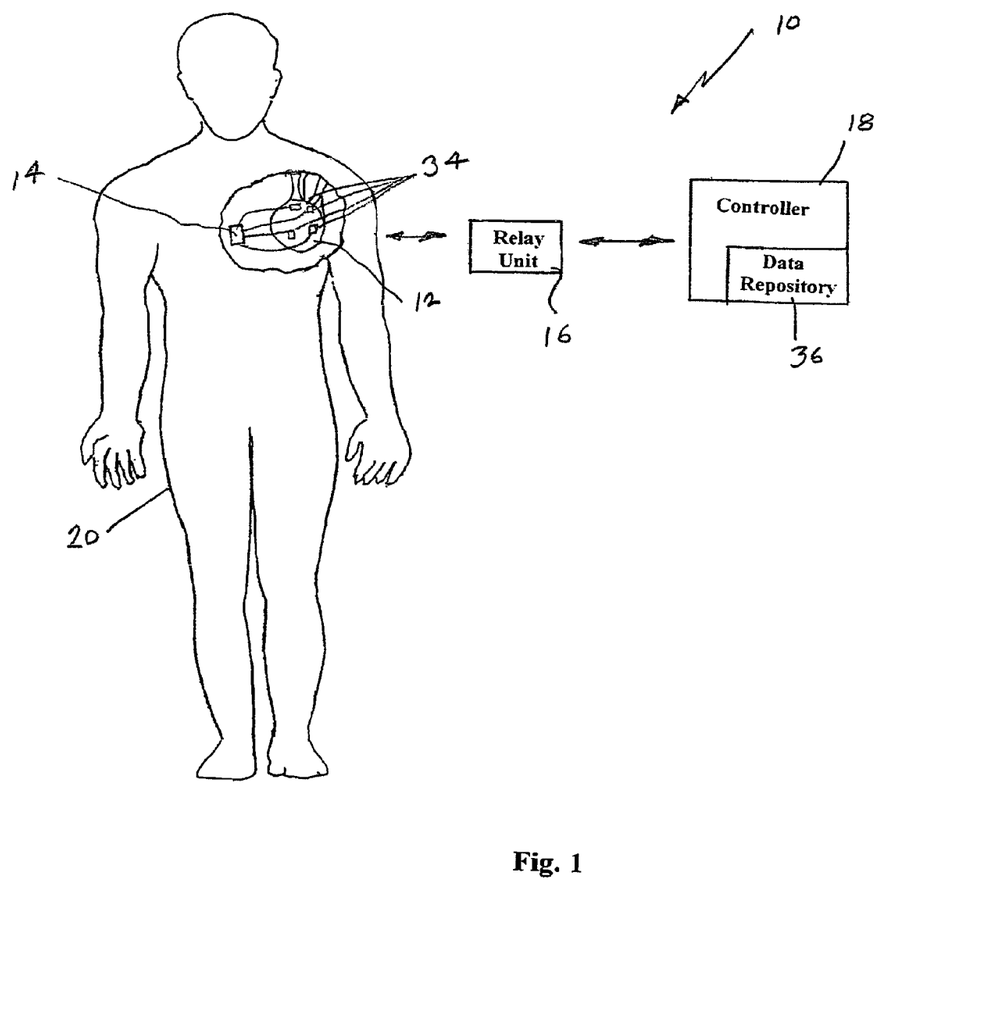
FIG. 1 is a diagram illustrating a system for monitoring a patient's heart, according to one embodiment of the present invention.
Figure 2:
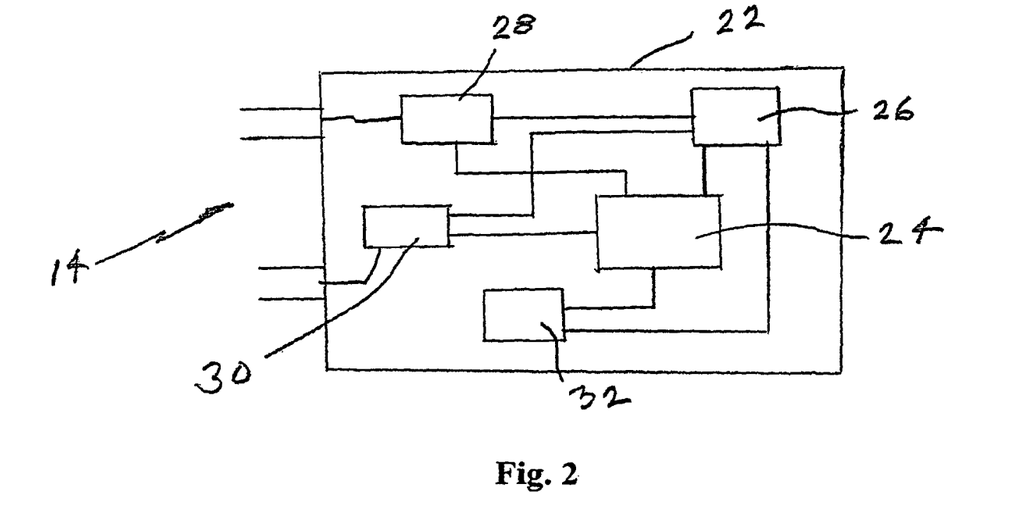
FIG. 2 is a block diagram illustrating a measuring unit, according to one embodiment of the present invention.

Referring to FIG. 1, there is illustrated a system 10 for monitoring the heart 12 of a heart transplant patient or a patient suffering congestive heart failure. The system 10 includes an implantable registering unit 14 for non-invasive monitoring of a patient's heart 12, a relay unit 16 for interrogating the registering unit, and a controller 18 for receiving data from the relay unit 16 corresponding to the patient's heart and analyzing the data. The registering unit 14 is structured to be implanted into the patient's body 20 and, thus, preferably includes a housing 22 constructed of a relatively rigid material that is biologically inert, such as titanium and silicone. As illustrated in FIG. 2, the registering unit 14 can include a controller 24, such as a computer, microprocessor, or central processing unit operating under software control, an energy source 26, a receiver 30, and a transmitter/antenna 32. The registering unit 14 can optionally include a generator 28 structured to provide electrical stimulus to the patient's heart, a therapeutic process commonly referred to as "pacing." The use of electrical stimuli to treat disorders such as bradyarrhythmias, or slow heart rhythms, and tachyarrhythmias, or fast heart rhythms, is well known to those skilled in the art and will not be further described herein. The energy source 26 is structured to provide electrical or thermal energy to the other components of the registering unit 14, including the controller 18, generator 28, receiver 30, and/or transmitter/antenna 32. The transmitter/antenna 32 is structured to communicate with the relay unit 16 electrically, such as through radio frequency communication, or optically. In one embodiment, the transmitter/antenna 32 includes an induction coil (not shown) that is structured to communicate with a corresponding induction coil (not shown) in the relay unit 16. Any commercially available pacemaker with appropriate software modifications can be used as the registering unit 14.

As illustrated in FIGS. 1 and 2, the controller 24 is in electrical communication with the patient's heart 12 via one or more sets or pairs of electrodes 34. According to one construction, as illustrated in FIG. 1, the system 10 includes two pairs of electrodes 34. The electrodes 34 can comprise any one of a number of commercially available epicardial (outside the surface of the heart) or endocardial (inside the heart) electrodes, as is well known to those skilled in the art. According to one embodiment, the electrodes 34 comprise screw-in epicardial bipolar IS I leads. The electrodes 34 preferably are attached to the heart 12 at the left and right ventricles, and left and right atriums. The electrodes 34 can be positioned at other areas about the patient's heart 12, depending on a variety of factors including, but not limited to, whether the patient is a heart transplant patient or suffering from congestive heart failure, the physical characteristics of the patients heart, or need for cardiac pacing. The electrodes 34 can be modified to include pressure sensors, which gauge vigor or degree of myocardial contraction.

The controller 18 can include a computer, microprocessor, or central processing unit operating under software control. As illustrated in FIG. 1, the controller 18 preferably comprises a data depository 36 comprising hardware and associated software for data storage. The data repository 36 is in operable communication with the controller 18 via appropriate wiring or circuitry (not shown). The data repository 36 is structured to receive and store in computer-readable memory data corresponding to the electrical signals received from the patient's heart 12. The relay unit 16 is structured to transmit to the controller 18 data corresponding to the electrical signals received from the patient's heart 12 and to receive instructions transmitted by the controller 18 and transmit these instructions to the controller 24 of the registering unit 14 via the transmitter/antenna 32.

According to one construction, the controller 18 is located at the same location as the relay unit 16 and the patient, such as at a medical care facility or office or at the patient's home. For example, the relay unit 16 can be connected in operable communication with the controller 18 through a serial port connection or through a USB connection. According to another construction, the controller 18 is disposed remotely from the relay unit 16 and the patient. According to this construction, the relay unit 16 comprises another controller, such as a computer, microprocessor, or central processing unit operating under software control, that is in operable communication with the controller 18 via a computer network, including, but not limited to, the interne, a local area network, a wide area network, a wireless network (such as satellite), a dial-up modem, etc., so that the relay unit 16 can communicate with the controller 18.

Advantageously, this later embodiment eliminates the need to have an analog/digital converter or demodulator at the patient testing center.

Referring to FIGS. 1 and 2, when monitoring a patient's heart 12, the controller 18, either automatically at predetermined intervals or pursuant to instructions from an operator, communicates instructions to controller 24 of the registering unit 14 via the communication link between the relay unit 16 and transmitter/antenna 32 of the registering unit 14, instructing the registering unit to initiate monitoring of the patient's heart. The controller 24 then instructs the receiver 30 to begin registering or sensing the electrical signals emitted by the patient's heart. Data corresponding to the electrical signals registered by the receiver 30 is communicated to the controller 24. The controller 24 communicates the data representing the electrical signals registered by the receiver 30 to the transmitter/antenna 32, which then communicates the data to the relay unit 16. The relay unit 16 in turn communicates the data to the controller 18 for analysis.

Figure 3:
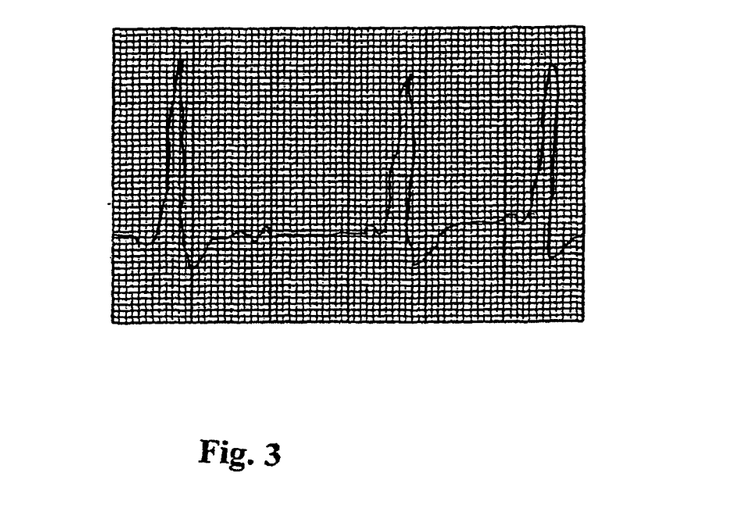
FIG. 3 is a diagram showing a digitized electrogram or template, according to one embodiment of the present invention.
Figure 4:
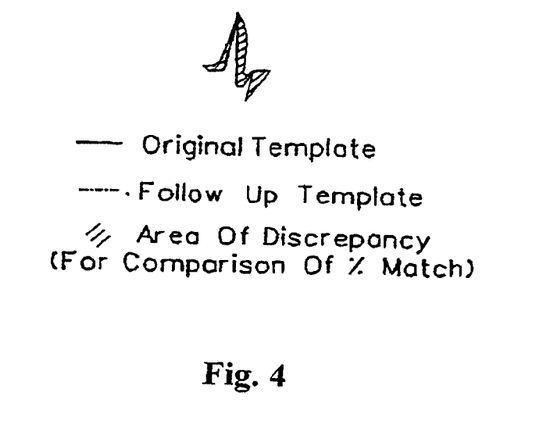
FIG. 4 is a diagram graphically illustrating a comparison of a first template, which corresponds to a registered electrical signal from a patient's heart, to a second template, which corresponds to a baseline electrical signal from the patient's heart, according to one embodiment of the present invention.

The controller 18 operating under associated software control allows precise discrimination of intracellular and extracellular myocardial dynamics, as well as volume changes and myocardial strength of contraction in the patient's heart 12. The controller 18 is structured to analyze the data received from the patient's heart 14 in several ways. According to one procedure, each time the controller 18 receives data corresponding to the electrical signals received by the registering unit 14 from the patient's heart 12, the controller 18 digitally creates or generates a graphical representation, such as a waveform, graph, or chart (referred to herein as a "template"), of a patient's intracardiac electrogram, such as the one illustrated in FIG. 3. For example, according to one form, the electrical signals received from the patient's heart comprise analog electrogram signals that are digitized by the controller 18 at 1 KHz with a 12-bit resolution and stored in the data repository 36 for later analysis. Preferably, a baseline electrical signal is registered using the above-referenced procedure to produce a template of the baseline electrical signal that is stored in the data repository 36 for later analysis. The baseline electrical signal can be obtained when the patient undergoes heart transplant, when the registering unit 14 is implanted, or at some other predetermined time.

The generation of the graphical representations by the controller 18 can include, but is not limited to: (1) individual beat identification (via peak detection algorithms); (2) Fourier decomposition of selected beats or beat sequences; (3) Fourier coefficient averaging and average signal reconstruction, assessing the average heart beat of the patient (as derived or computed from the data corresponding to the registered electrical signals received from the patient's heart 12, for critical time, area, derivative. and amplitude markers using standard techniques); (4) utilizing Fourier coefficients and average waveform markers as descriptors of the graphical representation and comparing them using either time-series or auto- and cross-correlation analysis techniques; (5) constructing a modified wavelet template and performing a critical match percent correlation; (6) transforming wavelets, which are fragments of a complete waveform, to identify frequency and/or scale components of a signal simultaneously with their location in time; (7) using wavelet transformation that entails scale analysis via creation of mathematical structures that provide varying time/frequency/amplitude slices of a waveform for analysis.

The analysis by the controller 18 of the digitized electrograms or templates for the baseline electrical signal and the registered electrical signal involves comparing the templates to determine whether a predetermined critical match-percent threshold between the templates has been exceeded. For example, the analysis can include a modified wavelet template construction and a critical match percent correlation. Wavelet transformation (WT) identifies frequency or scale components of a signal and simultaneously with its location in time. The transformation entails scale analysis via creation of mathematical structures that provide varying time/frequency/amplitude slices for analysis. Each transformation is a fragment of a complete waveform and is termed as "wavelet." Wavelets are optimal for approximating data with sharp discontinuities, such as myocardial electrograms. Since a percent wavelet match for a given heart rhythm is stable with regard to changes in body position and exercise over time, this algorithm offers greater sensitivity than conventional techniques, such as morphology algorithms (i.e., UPPRM), that analyze the amplitude of selected of a electrogram.

Figure 5:
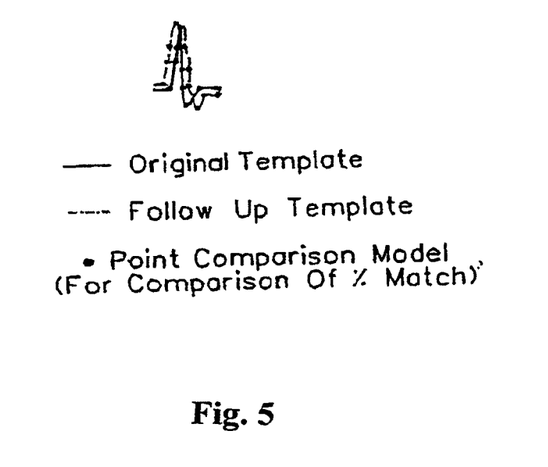
FIG. 5 is a diagram graphically illustrating a comparison of a first template, which corresponds to a registered electrical signal from a patient's heart, to a second template, which corresponds to a baseline electrical signal from the patient's heart, according to one embodiment of the present invention.
Figure 6:
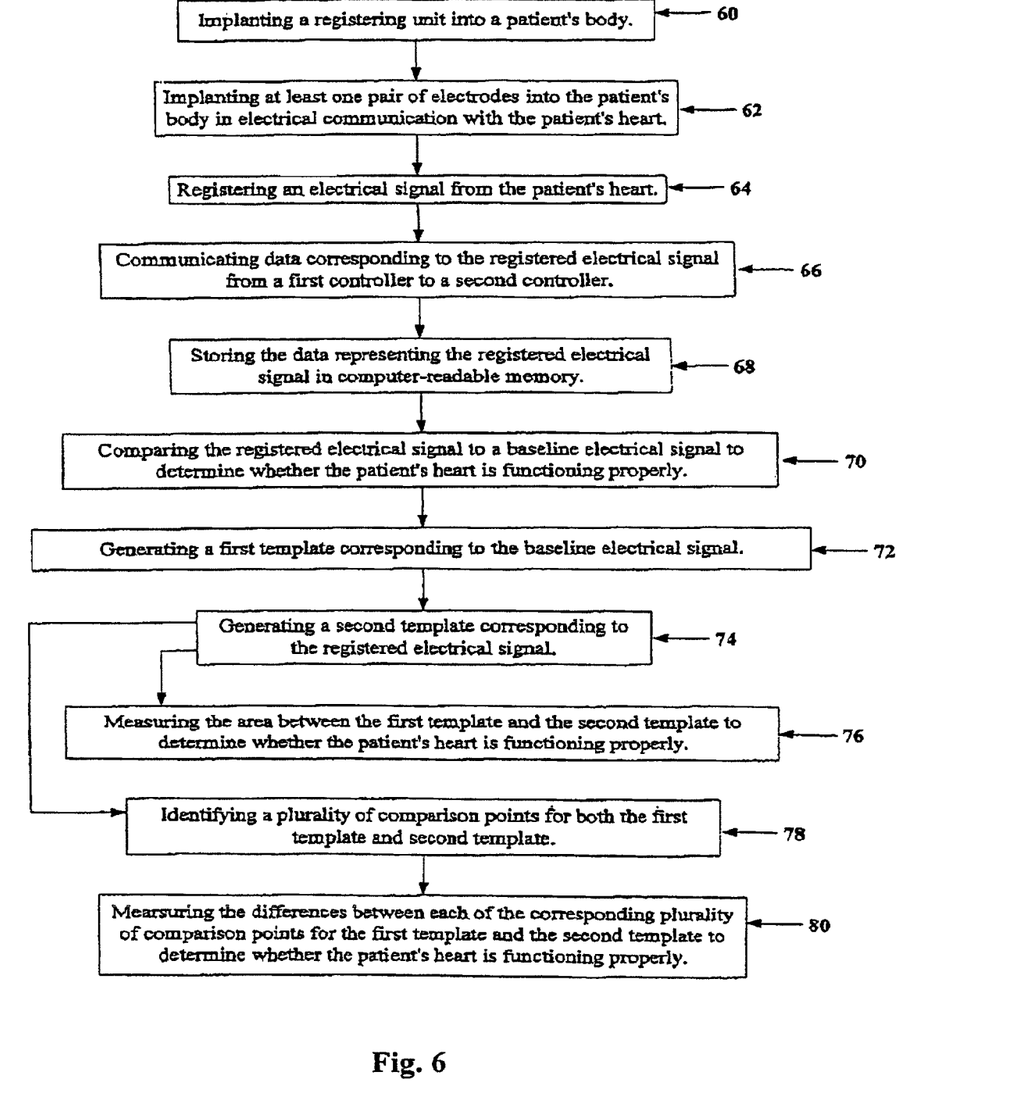
FIG. 6 is a flow chart illustrating a method of monitoring a patient's heart, according to one embodiment of the present invention.

According to one embodiment, as illustrated in FIG. 5, the templates for the baseline electrical signal and the registered electrical signal are compared by measuring the area of discrepancy between the templates and determining a comparison percentage match, which can then be used to access whether the patient's heart is functioning properly. According to another embodiment, as illustrated in FIG. 6, the comparison involves identifying a plurality of comparison points for the baseline template and identifying a plurality of comparison points for the template corresponding to the registered electrical signal. Each of the plurality of comparison points for the second template corresponding to one of the comparison points for the baseline template. Thereafter, a correlation of points in the template will provide a comparison percentage match between the two templates, which can then be used to access whether the patient's heart is functioning properly.

A critical match-percentage threshold under either method (i.e., a discrepancy in the match points) of over thirty percent (30%), or more preferably, twenty (20%), or still more preferably, ten percent (10%) would indicate acute heart rejection. Thus, if a subsequent template corresponding to an electrical signal received from the patient's heart 12 does not correlate to the baseline template, by greater than seventy percent (70%), more preferably greater than eighty percent (80%), and still more preferably greater than ninety percent (90%), then rejection is present. Early detection of rejection advantageously permits prompt initiation of life saving therapy.

The present invention also provides a method for monitoring a patient's heart. According to one embodiment, the method includes implanting a registering unit into a patient's body. See Block 60. At least one pair of electrodes is implanted into the patient's body in electrical communication with the patient's heart. See Block 62. The method includes registering an electrical signal from the patient's heart. See Block 64. Data corresponding to the registered electrical signal is communicated from a first controller to a second controller. See Block 66. In one embodiment, the data representing the registered electrical signal is stored in computer-readable memory. See Block 68.

The method includes comparing the registered electrical signal to a baseline electrical signal to determine whether the patient's heart is functioning properly. See Block 70. In one embodiment, the comparing step includes generating a first template corresponding to the baseline electrical signal. See Block 72. A second template corresponding to the registered electrical signal is generated. See Block 74. Thereafter, the area between the first template and the second template is measured to determine whether the patient's heart is functioning properly. See Block 76. In another embodiment, the comparing step includes identifying a plurality of comparison points for both the first template and second template. See Block 78. Each of the plurality of comparison points for the second template corresponds to one of the comparison points for the first template. The differences between each of the corresponding plurality of comparison points for the first template and the second template are then measured to determine whether the patient's heart is functioning properly. See Block 80.

FIGS. 1, 2 and 6 are block diagrams, flowcharts and control flow illustrations of methods, systems and program products according to the invention. It will be understood that each block or step of the block diagrams, flowcharts and control flow illustrations, and combinations of blocks in the block diagrams, flowcharts and control flow illustrations, can be implemented by computer program instructions. These computer program instructions may be loaded onto a computer or other programmable apparatus to produce a machine, such that the instructions which execute on the computer or other programmable apparatus create means or devices for implementing the functions specified in the block diagrams, flowcharts or control flow block(s) or step(s). These computer program instructions may also be stored in a computer-readable memory that can direct a computer or other programmable apparatus to function in a particular manner, such that the instructions stored in the computer-readable memory produce an article of manufacture, including instruction means or devices which implement the functions specified in the block diagrams, flowcharts or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagrams, flowcharts or control flow block(s) or step(s).

Accordingly, blocks or steps of the block diagrams, flowcharts or control flow illustrations support combinations of means or devices for performing the specified functions, combinations of steps for performing the specified functions and program instruction means or devices for performing the specified functions. It will also be understood that each block or step of the block diagrams, flowcharts or control flow illustrations, and combinations of blocks or steps in the block diagrams, flowcharts or control flow illustrations, can be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for monitoring a patient's heart, comprising:
   a registering unit comprising a first controller in electrical communication with the patient's heart, said first controller being configured to register an electrical signal emitted by the patient's heart; and
   a second controller in operable communication with said first controller, said second controller being configured to receive data from said first controller corresponding to the registered electrical signal; to generate a registered template comprising a digital graphical representation of an intracardiac electrogram for the registered electrical signal; and to compare the registered template to a baseline template comprising a digital graphical representation of an intracardiac electrogram for a baseline electrical signal emitted by the patient's heart to determine whether the patient's heart is functioning properly, wherein the second controller is adapted to compare the baseline template and the registered template through a wavelet transformation in which the templates are transformed to create one or more wavelets in the form of corresponding fragments of the templates, the second controller being adapted to compare one or more registered wavelets to one or more corresponding baseline wavelets to determine whether the patient's heart is functioning properly.

2. The system of claim 1, wherein said registering unit further comprises a transmitter in operable communication with said second controller.

3. The system of claim 1, further comprising a relay unit independent of said first controller and said second controller and configured to communicate with said first controller and said second controller, said relay unit being configured to receive data from said first controller corresponding to the registered electrical signal and to transmit the received data to said second controller.

4. The system of claim 3, wherein the relay unit is configured to wirelessly communicate with said registering unit.

5. The system of claim 1, wherein said second controller is located remotely from said registering unit.

6. The system of claim 1, wherein said second controller includes a data repository for storing data corresponding to the registered template and data corresponding to the baseline template of the patient's heart.

7. The system of claim 1, further comprising a plurality of electrodes in electrical communication with said registering unit and configured to be coupled directly to the heart.

8. The system of claim 1, wherein said second controller is configured to determine whether a predetermined critical match-percent threshold has been exceeded based on a comparison of the registered template and the baseline template.

9. The system of claim 8, wherein the critical match-percent threshold comprises at least 70% correlation between the registered template and the baseline template, wherein a critical-match percent threshold less than 70% indicates that the heart is not functioning properly.

10. The system of claim 8, wherein the critical match-percent threshold comprises at least 80% correlation between the registered template and the baseline template, wherein a critical-match percent threshold less than 80% indicates that the heart is not functioning properly.

11. The system of claim 8, wherein the critical match-percent threshold comprises at least 90% correlation between the registered template and the baseline template, wherein a critical-match percent threshold less than 90% indicates that the heart is not functioning properly.

12. The system of claim 1, wherein said second controller is configured to measure the area between the registered template and the baseline template to determine whether the patient's heart is functioning properly.

13. The system of claim 1, wherein said second controller is configured to identify a plurality of comparison points for the registered template and to identify a plurality of comparison points for the baseline template, each of the plurality of comparison points for the baseline template corresponding to one of the comparison points for the registered template, and wherein said second controller is configured to measure differences between each of the corresponding plurality of comparison points for the registered template and the baseline template to determine whether the patient's heart is functioning properly.

14. The system according to claim 1, wherein said registering unit further comprises a housing of biologically inert material for housing said first controller.

15. The system of claim 1, wherein said second controller is configured to calculate a quantifiable difference between the registered template and the baseline template based on the comparison between the templates in order to determine whether the patient's heart is functioning properly.

16. The system of claim 1, wherein said second controller is configured to compare the registered template to the baseline template following a heart transplant in order to determine whether the patient's transplanted heart is being rejected.

17. The system of claim 1, wherein the second controller determines a percent wavelet match between the registered wavelets and baseline wavelets to determine whether the patient's heart is functioning properly.

18. The system of claim 1, wherein the second controller performs one of an area of discrepancy determination and a comparison of corresponding points determination of the registered wavelets and baseline wavelets to determine whether the patient's heart is functioning properly.

19. The system of claim 1, wherein the wavelet transformation comprises identifying frequency and scale components of the signals represented graphically by the templates simultaneously with its location in time, the transformation further comprising scale analysis via creation of mathematical structures that provide varying time, frequency, and amplitude slices for comparison to determine whether the patient's heart is functioning properly.

* * * * *